United States Patent [19]

McAlpine et al.

[11] 4,423,210
[45] Dec. 27, 1983

[54] INTERMEDIATES FOR THE PREPARATION OF 3-DEMETHOXYFORTIMICINS

[75] Inventors: James B. McAlpine, Libertyville; Ronald E. Carney, Gurnee, both of Ill.

[73] Assignee: Abbott Laboratories, North Chicago, Ill.

[21] Appl. No.: 366,797

[22] Filed: Apr. 9, 1982

[51] Int. Cl.³ .................... A61K 31/71; C07H 15/22
[52] U.S. Cl. .................................... 536/16.1; 424/180
[58] Field of Search .................................... 536/16.1

[56] References Cited

U.S. PATENT DOCUMENTS 4,124,756 11/1978 Martin et al. .................... 536/16.1
4,187,297 2/1980 Martin et al. .................... 536/16.1

Primary Examiner—Johnnie R. Brown
Attorney, Agent, or Firm—Dennis K. Shelton

[57] ABSTRACT

Disclosed herein are fortimicin derivatives represented by the formula:

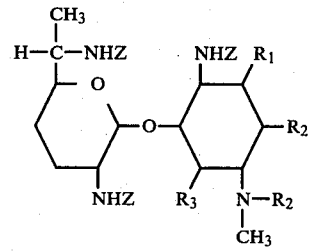

wherein $R_z$ is a monocyclicaryloxycarbonyl amine protecting group, or is loweralkyl, hydroxyloweralkyl, loweracyl, hydroxyloweracyl, or a monocyclicaryloxycarbonyl-protected aminoloweralkyl, diaminoloweralkyl, N-loweralkylaminoloweralkyl, N,N-diloweralkylaminoloweralkyl, aminohydroxyloweralkyl, N-loweralkylaminohydroxy-loweralkyl, N,N-diloweralkylaminohydroxyloweralkyl, aminoloweracyl, diaminoloweracyl, N-loweralkylaminoloweracyl, N,N-diloweralkylaminoloweracyl, or aminohydroxyloweracyl; $R_1$ is hydroxy or loweracyloxy; $R_2$ is hydrogen, hydroxy or $-OR_4$, wherein $R_4$ is tert-butyldimethylsilyl or thiocarbonylimidazoyl; or $R_1$ and $R_2$ can be taken together to form

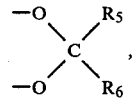

wherein $R_5$ and $R_6$ are loweralkyl; $R_3$ is hydroxy or loweracyloxy; and z is a monocyclicaryloxycarbonyl amine protecting group. The compounds are useful as intermediates in the preparation of 3-demethoxyfortimicins.

12 Claims, No Drawings

INTERMEDIATES FOR THE PREPARATION OF 3-DEMETHOXYFORTIMICINS

BACKGROUND OF THE INVENTION

The present invention relates to 3-demethoxyfortimicin A, 3demethoxyfortimicin B, 4-N-substituted derivatives of 3-demethoxyfortimicin B, and their pharmaceutically acceptable salts, to intermediates useful in the preparation of these compounds, and to compositions comprising these compounds and pharmaceutically acceptable carriers or diluents.

The fortimicins are a relatively new class of aminoglycoside antibiotics which are useful in the treatment of susceptible bacterial infections. Fermentation produced fortimicins include fortimicin A, disclosed in U.S. Pat. No. 3,976,768; fortimicin B, disclosed in U.S. Pat. No. 3,931,400; and fortimicin C, disclosed in U.S. Pat. Nos. 4,048,015 and 4,097,428. Other fermentation fortimicin factors have also been isolated.

Once an aminoglycoside antibiotic has been in clinical use for a period of time, resistant microorganisms may develop. In many cases, the resistance is R-factor mediated and is attributed to the ability of the bacteria to enzymatically modify the amino or hydroxyl groups of the aminoglycoside antibiotics and thereby reduce or eliminate their antibacterial properties. Thus, there is also a need for new entities which can be held in reserve to combat strains which have become resistant to treatment by the clinically used antibiotics. In the past, it has been found that the antibacterial and pharmacological properties of many naturally produced aminoglycoside antibiotics can be altered by structural modifications. As an example, certain chemical modifications in the gentamycin and kanamycin family of aminoglycoside antibiotics provide structures which are less toxic than the parent antibiotic. Further, in the same series, certain modifications alter the antibacterial spectrum advantageously either by increasing the intrinsic activity or increasing activity against resistant strains.

It has been previously determined that certain chemical modification of the parent fortimicins can also result in derivative compounds which exhibit increased antibacterial activity with respect to particular microorganisms, reduced toxicity, or equivalent of reduced activity, but nevertheless are useful as reserve antibiotics in the event resistant strains develop after a period of clinical use of one or more of the fortimicins. For example, 4-N-acyl and -alkyl derivatives of fortimicin B and techniques for forming these compounds are disclosed in U.S. Pat. Nos. 4,091,032; 4,155,902; 4,173,564; 4,174,312; 4,220,775 and 4,231,924; the disclosures of which are specifically incorporated herein by reference; and others. The fortimicin compounds have also been demethylated at the 3-position to provide useful derivatives. For example, 3-O-demethylfortimicins are disclosed in U.S. Pat. Nos. 4,124,756; 4,187,297; 4,220,756; 4,230,848; 4,242,503; 4,251,516 and 4,293,689.

While a number of fortimicin derivatives have been made to date, and valuable therapeutic agents have been identified, it is desirable to obtain new fortimicin antibiotics which exhibit a broader or different antibacterial spectrum, less toxicity, oral activity, or other desirable properties, or which can be held in reserve and used to treat infections caused by organisms which become resistant to other fortimicin therapy.

The present invention relates to novel 3-demethoxyfortimicins which exhibit antibacterial activity. More specifically, the present invention relates to 3-demethoxyfortimicin A, 3-demethoxyfortimicin B, and 4-N-substituted-3-demethoxyfortimicin B, to intermediates and processes useful in the production of these novel compounds, and to compositions comprising these compounds and a pharmaceutically acceptable carrier or diluent.

DETAILED DESCRIPTION OF THE INVENTION

The 3-demethoxyfortimicin compounds of the invention differ from fortimicin A, fortimicin B, and fortimicin B derivatives, in their absence of a methoxy group at the 3- position of the cyclitol ring of the aminoglycoside. These 3-demethoxyfortimicins can be represented by the following structural formula:

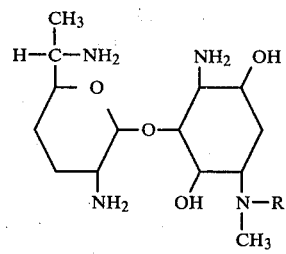

wherein R is hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, loweracyl, aminoloweracyl, diaminoloweracyl, hydroxyloweralkyl, N-loweralkylaminoloweralkyl, N,N-diloweralkylaminoloweracyl, or aminohydroxyloweracyl, and the pharmaceutically acceptable salts thereof.

Intermediates of the invention useful in preparing the 3-demethoxyfortimicins of formula I can be represented by the structural formula:

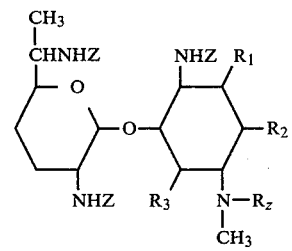

wherein $R_z$ is R as defined in formula I or a monocyclicaryloxycarbonylamine protecting group, or when R is an amino containing group then $R_z$ is monocyclicaryloxycarbonyl-protected R; $R_1$ is hydroxy or loweracyloxy; $R_2$ is hydrogen, or $-OR_4$, wherein $R_4$ is tert-butyl- dimethylsilyl or thiocarbonylimidazoyl; or $R_1$ and $R_2$ can be taken together to form

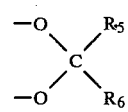

wherein $R_5$ and $R_6$ are loweralkyl; $R_3$ is hydroxy or loweracyloxy; and Z is a monocyclicaryloxycarbonyl amine protecting group.

The term "loweralkyl," as used herein, refers to straight or branched chain alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 2-methylpentyl, n-heptyl and the like.

The term "loweracyl" as used herein refers to acyl groups represented by the formula $$-\overset{O}{\underset{\|}{C}}-R_7,$$

wherein $R_7$ is loweralkyl, as defined above. Representative loweracyl groups useful in the invention include acetyl, propionyl, butyryl, valeryl and the like.

The term "loweracyloxy" as used herein refers to acyloxy groups of the formula $-O-R_8$, wherein $R_8$ is loweracyl, as defined above.

The terms "aminoloweracyl," "diaminoloweracyl," etc., include the naturally occurring aminoacids such as glycyl, valyl, alanyl, sarcosyl, leucyl, isoleucyl, prolyl, seryl, and the like as well as other amino-substituted lower acyl groups such as 2-hydroxy-4-aminobutyryl. The aminoacids residue included in the above terms can be in the L- or D- configurations or a mixture thereof, with the exception of glycyl.

The term "monocyclicaryloxycarbonyl" as used herein refers to protecting groups such as benzyloxycarbonyl, paramethylbenzyloxycarbonyl, paramethoxybenzyloxycarbonyl or orthonitrobenzyloxycarbonyl which are commonly used as N-protecting groups in peptide synthesis and in other areas where N-protection is required.

The term "pharmaceutically acceptable salts," as used herein, refers to the nontoxic acid addition salts of the compounds of this invention. These salts can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salts of this invention can be per-N-salts.

The 3-demethoxyfortimicin compounds of the invention may be prepared from a per-N-protected fortimicin such as tetra-N-protection fortimicin A, according to the following reaction scheme:

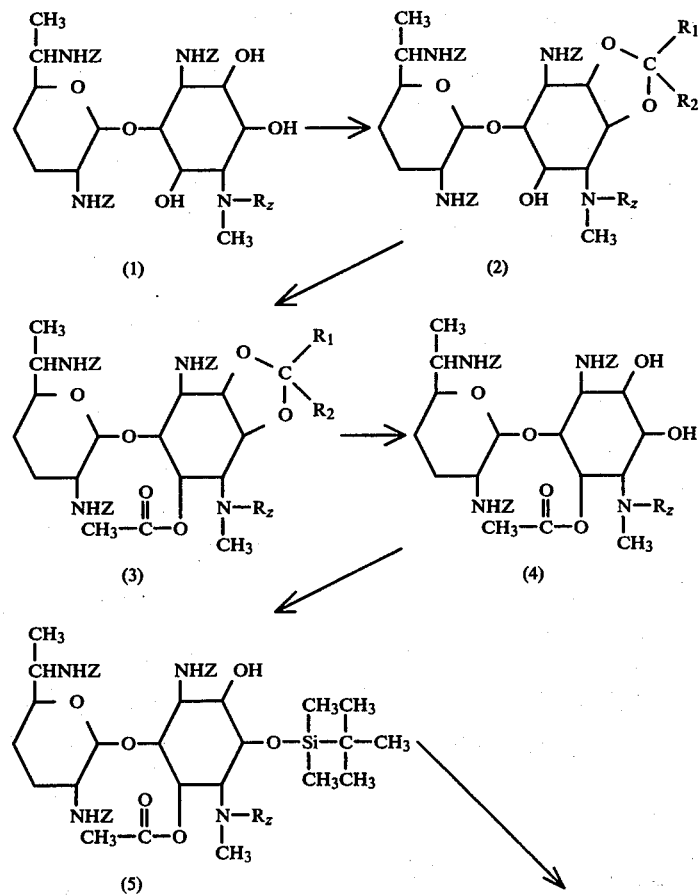

-continued

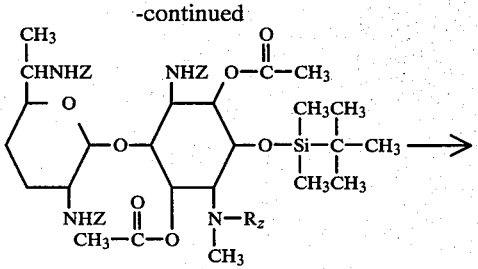
(6)

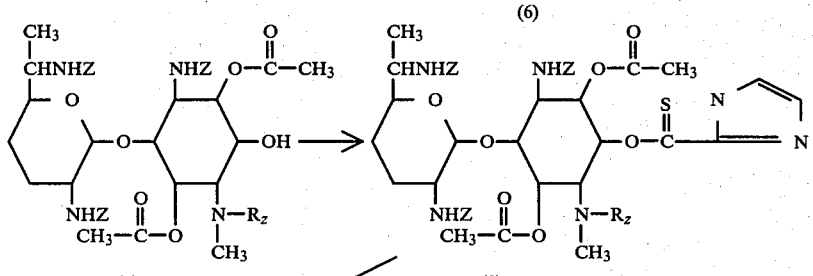
(7)    (8)

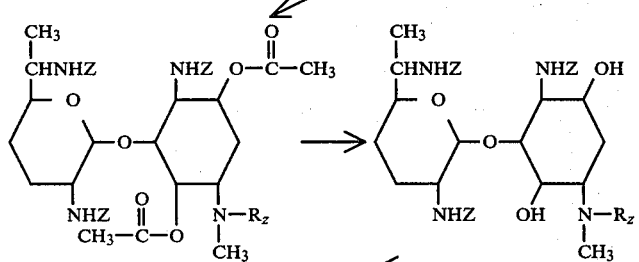
(9)    (10)

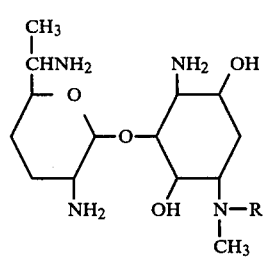
(11)

In the foregoing reaction sequence, per-N-protected-3-O-demethylfortimicin (1), such as tetra-N-benzyloxycarbonyl-3-O-demethylfortimicin A (see, for example, U.S. Pat. No. 4,124,756), is converted to per-N-protected-3-O-demethylfortimicin-2,3-acetonide (2) by dissolving the starting material in an aldehyde or ketone such as acetone and treatment with ferric chloride in silica gel. The 2,3- acetonide is then acetylated at the 5-position to form tetra-N-protected-3-O-demethyl-5-O-acetylfortimicin-2,3-acetonide (3), such as by treatment with acetic anhydride and an organic base in a suitable solvent, and then treated with a mineral acid in methanol to form per-N-protected-3-O-demethyl-5-O-acetyl-fortimicin (4). Dissolution of (4) in dimethylformamide and treatment with tert-butyldimethylsilylchloride in the presence of a catalyst results in the formation of per-N-protected-3-O-demethyl-5-O-acetyl-fortimicin-3-O-tert-butyldimethyls ilylether (5) which is converted to the corresponding 2,5-bisacetyl intermediate (6) by treatment with acetic anhydride and an organic base in a suitable solvent. The silylether group is cleaved with tetrabutylammonium fluoride in the presence of acetic acid to form per-N-protected-3-O-demethyl-2,5-bis-fortimicin (7), which is reacted with N,N'-thiocarbo-nyldiimidazole in a suitable solvent to form per-N-protected-3-O-demethyl-2,5-bisacetylfortimicin-3-O-thiocarbonylimidazolide (8). The 3-O-thiocarbonyl-imidazolide (8) is refluxed with tri-N-butyltinhydride in a suitable solvent to form the N- and O-protected 3-demethoxyfortimicin intermediate (9). The protected compound is then O-deprotected by treatment with sodium ethoxide and N-deprotected by hydrogenation, as is known in the art, to form the desired end product, 3-demethoxyfortimicin (11).

When R in the foregoing reaction sequence is hydrogen, the resulting 1,2',6'-tri-N-protected 3-demethoxyfortimicin B (10) can be acylated with N-(N-benzyloxycarbonylglycyloxy) succinimide to give 1,2',6'2''-tetra-N-protected-3-demethoxyfortimicin A (10). Catalytic hydrogenation of 1,2',6',2''-tetra-N-protected 3-demethoxyfortimicin A produces 3-demethoxyfortimicin A, which can be isolated as a pharmaceutically acceptable salt, as is known in the art. Alternatively, 3-demethoxyfortimicin A can be produced directly from the foregoing reaction sequence by using tetra-N-protected-3-O-demethylfortimicin A as the starting material (1). The per-N-protected-fortimicin B intermediate can also be alkylated and acylated at the 4-N-position to produce 4-N-alkyl or 4-N-acyl-substituted-3-demethoxyfortimicin B by 4-N-alkylation and 4-N-acylation techniques well known in the fortimicin art, such as by techniques referred to in the issued patents cited supra.

The foregoing reaction scheme may be better understood in connection with the following examples:

EXAMPLE 1

Tetra-N-benzyloxycarbonyl-3-O-demethylfortimicin A-2,3-acetonide

To 10 g. of tetra-N-benzyloxycarbonyl-3-O-demethylfortimicin A dissolved in 350 ml. of acetone is added 200 g. of silica gel impregnated with 10% by weight ferric chloride. The silica gel is maintained in suspension in the mixture by stirring at room temperature overnight. The mixture is filtered to remove the silica gel and then poured into 800 ml. of a 10% sodium bicabonate solution. The resulting aqueous suspension is extracted with two 250 ml. portions of methylene chloride. The extracts are combined and dried over magnesium sulfate under reduced pressure to produce 10 g. of tetra-N-benzyloxycarbonyl-3-O-demethylfortimicin A-2,3-acetonide.

Analysis Calculated for $C_{51}H_{61}N_5O_{14}$: C, 63.27; H, 6.35; N, 7.23. Found: C, 63.28; H, 6.42; N, 7.24.

EXAMPLE 2

Tetra-N-benzyloxycarbonyl-3-O-demethyl-5-O-acetyl-fortimicin A-2,3-acetonide

To 10 g. of tetra-N-benzyloxycarbonyl-3-O-demethylfortimicin A-2,3-acetonide dissolved in 250 ml. of anhydrous pyridine is added 15 ml. of acetic anhydride. The resulting mixture is stirred at room temperature for 48 hours. The solvent is then removed under reduced pressure to yield 10.3 g. of tetra-N-benzyloxycarbonyl-3-O-demethyl-5-O-acetylfortimicin A-2,3-acetonide.

Analysis Calculated for $C_{53}H_{63}N_5O_{15}$: C, 63.02; H, 6.28; N, 6.93. Found: C, 62.81; H, 6.21; N, 6.70.

EXAMPLE 3

Tetra-N-benzyloxycarbonyl-3-O-demethyl-5-O-acetyl-fortimicin A 30.4 g. of tetra-N-benzyloxycarbonyl-3-O-demethyl-5-O-acetylfortimicin A is dissolved in 250 ml. of a solution of 0.5 N sulfuric acid in methanol and the mixture is stirred at room temperature overnight. The mixture is mixed with 2.5 L. of a 5% aqueous sodium bicarbonate solution and the product is extracted with two 500 ml portions of methylene chloride. The extracts are then combined and dried over anhydrous magnesium sulfate under reduced pressure to yield 28 g. of tetra-N-benzyloxycarbonyl-3-O-demethyl-5-O-acetylfortimicin A.

Analysis Calculated for $C_{50}H_{59}N_5O_{15}$: C, 61.90; H, 6.13; N, 7.22. Found: C, 61.15; H, 6.13; N, 7.15.

EXAMPLE 4

Tetra-N-benzyloxycarbonyl-3-O-demethyl-5-O-acetyl-fortimicin A-3-O-tert-butyldimethylsilylether To 25 g. of tert-N-benzyloxycarbonyl-3-O-demethyl-5-O-acetylfortimicin A dissolved in 200 ml. of anhydrous dimethylformamide is added 8.75 g. tert-butyldimethylsilylchloride and 5.1 g. of imidazole. The reaction mixture is stirred for 48 hours at room temperature and then extracted with two 500 ml portions of methylene chloride. The extracts are combined and dried over anhydrous magnesium sulfate under reduced pressure. The resulting residue is chromatographed on a 7×70 cm. column of packed silica gel and eluted with a solvent system composed of ethylacetate and hexane (60:40 (v/v)) to yield 8.9 g. of tetra-N-benzyloxycarbonyl-3-O-demethyl-5-O-acetylfortimicin A-2-)-tert-butyldimethylsilylether and 11.7 g. of tetra-N-benzyloxycarbonyl-3-O-demethyl-5-O-acetylfortimicin A-3-O-tert-butyldimethylsilylether.

Analysis Calculated for $C_{56}H_{73}N_5O_{15}S$: C, 62.03; H, 6.73; N, 6.46. Found: C, 61.68; H, 6.69; N, 6.33.

EXAMPLE 5

Tetra-N-benzyloxycarbonyl-3-O-demethyl-2,5-bisacetylfortimicin A-3-O-tert-butyldimethylsilylether To 2.5 g. of tetra-N-benzyloxycarbonyl-3-O-demethyl-5-acetylfortimicin A-3-O-tert-butyldimethylsilylether dissolved in 40 ml. of anhydrous pyridine is added 4 ml. of acetic anhydride. The resulting mixture is stirred at room temperature overnight. The solvent is removed under reduced pressure and the residue is chromatographed on a 2.5×70 cm. column of packed silica gel eluted with a solvent system composed of ethylacetate and hexane (60:40 (v/v) to yield 2.2 g. of tetra-N-benzyloxycarbonyl-3-O-demethyl-2,5-bisacetylfortimicin A-3-O-tert-butyl-dmethylsilylether.

Analysis Calculated for $C_{58}H_{75}N_5O_{15}Si$: C, 61.84; H, 6.71; N, 6.25. Found: C, 61.48; H, 6.73; N, 6.29.

EXAMPLE 6

Tetra-N-benzyloxycarbonyl-3-O-demethyl-2,5-bisacetylfortimicin A

To 2.0 g. of tetra-N-benzyloxycarbonyl-3-O-demethyl-2,5-bisacetylfortimicin A-3-O-tert-butyldimethylsilylether in 20 ml. of tetrahydrofuran is added 8 ml. of 1 M tetrabutylammonium fluoride in tetrahydrofuran and 4 ml. of 1 M acetic acid in tetrahydrofuran. The resulting mixture is stirred at room temperature overnight and then mixed with 300 ml. of distilled water. The mixture is extracted with two 100 ml portions of methylene chloride. The extracted portions are combined and dried over anhydrous magnesium sulfate under reduced pressure. The residue is chromatographed on a 2.2×35 cm. column of packed silica gel eluted with a solvent system composed of ethylacetate-ethanol [(99:1 (v/v)] to yield 1.6 g. of tetra-N-benzyloxycarbonyl-3-O-demethyl-2,5-bisacetylfortimicin A.

Analysis Calculated for $C_{52}H_{61}N_5O_{16}$: C, 61.70; H, 6.07; N, 6.92. Found: C, 61.51; H, 6.01; N, 6.86.

EXAMPLE 7

Tetra-N-benzyloxycarbonyl-3-O-demethyl-2,5-bisacetylfortimicin A-3-O-thiocarbonylimidazolide To 2.1 g. of tetra-N-benzyloxycarbonyl-3-O-demethyl-2,5-bisacetylfortimicin A in 35 ml. of dichloroethane is added 1 g. of N,N'-thiocarbonyldiimidazole. The resulting mixture is heated at reflux for 2 hours and then dried under reduced pressure. The residue is chromatographed on a 2.5×65 cm. column of packed silica gel eluted with a solvent system composed of ethylacetate and hexane (4:1 (v/v)) to yield 1.8 g. of tetra-N-benzyloxycarbonyl-3-O-demethyl-2,5-bisacetylfortimicin A-3-O-thiocarbonylimadazolide.

Analysis Calculated for $C_{56}H_{63}N_7O_{16}S$: C, 59.93; H, 5.66; N, 8.74; S, 2.85. Found: C, 60.12; H, 5.78; N, 8.78; S, 3.17.

EXAMPLE 8

Tetra-N-benzyloxycarbonyl-2,5-bisacetyl-3-demethoxyfortimicin A

To a stirred refluxing solution of 1.7 ml. of tri-N-butyltinhydride and 100 ml. of dioxane, under a nitrogen atmosphere is added dropwise a solution of 1.7 g. of tetra-N-benzyloxycarbonyl-3-O-demethyl-2,5-bisacetylfortimicin A-3-O-thiocarbonylimidazolide in 50 ml. of dioxane. After refluxing for 2.5 hours, the solution is dried under reduced pressure and the residue is chromatographed on a 2.5×60 cm. column of packed silica gel eluted with a solvent system composed of ethylacetate and hexane (3:2 (v/v)) to yield 0.85 g. of tetra-N-benzyloxycarbonyl-2,5-bisacetyl-3-desmethoxyfortimicin A.

Analysis Calculated for $C_{52}H_{61}N_5O_{15}$: C, 62.70; H, 6.17; N, 7.03. Found: C, 62.80; H, 6.28; N, 6.99.

EXAMPLE 9

Tetra-N-benzyloxycarbonyl-3-desmethoxyfortimicin A

To 145 mg. of tetra-N-benzyloxycarbonyl-2,5-bisacetyl-3-demethoxyfortimicin A in 7 ml. of methanol is added 30 mg of sodium ethoxide. The resulting mixture is stirred for 30 minutes at room temperature and then mixed with 50 ml. of distilled water. The solution is extracted with two 25 ml portions of methylene chloride. The extracts are combined and dried over anhydrous magnesium sulfate under reduced pressure to yield 110 mg. of tetra-N-benzyloxycarbonyl-3-demethoxyfortimicin A.

Analysis Calculated for $C_{48}H_{57}N_5O_{13}$: C, 63.21; H, 6.30; N, 7.68. Found: C, 62.91; H, 6.20; N, 7.57.

EXAMPLE 10

3-Demethoxyfortimicin A tetrahydrochloride 112 mg. of tetra-N-benzyloxycarbonyl-3-demethoxyfortimicin A is dissolved in 100 ml. of 0.024 N methanolic hydrochloric acid and hydrogenated under 3 atmospheres of hydrogen in the presence of 112 mg. of palladium on carbon catalyst for four hours. The catalyst is removed by filtration and the solvent is evaporated under reduced pressure. Residual hydrochloric acid is removed by co-distillation with methanol under reduced pressure to yield 70 mg. of 3-demethoxyfortimicin A tetrahydrochloride.

The carbon magnetic resonance spectra of the compounds produced in Examples 1-9 are recorded in hexadeuteriodimethylsulfoxide and that of Example 10 in deuterium oxide, and are shown in Table I as the ppm downfield shift from tetramethylsilane of the fortimicin A skeletal carbon atoms:

TABLE I

| | CARBON MAGNETIC RESONANCE SPECTRA | | | | | | | | | | |
|---|---|---|---|---|---|---|---|---|---|---|---|
| | Example No. | | | | | | | | | | |
| | | | | | | | | | | 10 | |
| | 1 | 2 | 3 | 4 | 5 | 6 | 7 | 8 | 9 | HCl Salt | Pd/0.5 |
| C-1' | 94.1 | 94.8 | 95.9 | 95.9 | 96.0 | 95.8 | 94.6 | 95.9 | 95.8 | 95.2 | 100.0 |
| C-2' | 49.6 | 49.6 | 49.6 | 49.6 | 49.6 | 49.6 | 49.7 | 49.6 | 49.7 | 49.5 | 50.8 |
| C-3' | 23.2 | 22.9 | 23.0 | 22.9 | 22.8 | 23.0 | 22.7 | 23.2 | 23.4 | 21.6 | 27.3 |
| C-4' | 26.8 | 26.1 | 26.1 | 26.1 | 26.2 | 26.2 | 26.7 | 26.2 | 26.2 | 26.0 | 27.3 |
| C-5' | 71.2 | 70.7 | 70.9 | 72.1 | 72.1 | 72.5 | 72.4 | 71.5 | 69.9 | 70.8 | 74.2 |
| C-6' | 49.6 | 49.2 | 49.4 | 49.4 | 49.4 | 49.4 | 49.7 | 49.3 | 49.3 | 48.0 | 50.2 |
| C—CH₃ | 17.6 | 16.7 | 16.6 | 16.8 | 16.9 | 16.9 | 17.0 | 16.8 | 16.9 | 15.2 | 18.0 |
| C-1 | 54.1 | 54.0 | 54.6 | 56.6 | 57.1 | 52.1 | 53.7 | 51.8 | 53.6 | 52.9 | 55.1 |
| C-2 | 74.8 | 74.4 | 72.8 | 73.6 | 71.3 | 68.0 | 67.5 | 69.8 | 68.3 | 67.4 | 72.0 |
| C-3 | 72.4 | 74.2 | 64.3 | 64.6 | 67.9 | 64.8 | 78.3 | 25.6 | 27.2 | 26.3 | 26.8 |
| C-4 | 55.5 | 52.1 | 52.3 | 53.3 | 50.9 | 52.1 | 53.0 | 45.5 | 47.8 | 51.8 | 59.1 |
| C-5 | 69.7 | 69.6 | 69.7 | 69.6 | 69.5 | 69.9 | 69.2 | 69.8 | 69.9 | 69.1 | 69.2 |
| C-6 | 79.0 | 75.4 | 73.6 | 73.6 | 73.3 | 72.5 | 73.1 | 72.6 | 76.4 | 74.9 | 82.9 |
| NCH₃ | 32.0 | 29.5 | 30.0 | 30.4 | 30.7 | 30.2 | 33.1 | 29.8 | 30.5 | 31.9 | 32.3 |
| Gly—CH₂ | 42.4 | 42.3 | 42.0 | 42.0 | 41.4 | 42.2 | 42.1 | 42.2 | 42.3 | 41.3 | 43.2 |
| Gly—CO | 167.6 | 169.0 | 168.8 | 168.8 | 168.8 | 168.9 | 168.9 | 168.5 | 168.0 | 167.9 | |

EXAMPLE 11

Antibiotic Activity

The in vitro activity of 3-demethoxyfortimicin A of Example 10 is determined by a two-fold dilution test using 10 ml. of Mueller-Hinton agar per Petri plate. The agar plates are innoculated with approximately $1 \times 10^5$ of the test organisms indicated in Table II, delivered to the agar surface by a Steers replicator. The innoculated plates are incubated for 24 hours at 35° C. in the presence of varying concentrations of 3-demethoxyfortimicin A tetrahydrochloride of Example 10 or fortimicin A sulfate as a comparative antibiotic. The minimum inhibitory concentrations (MIC) of the antibiotics are shown in Table II, expressed as ug/ml.

TABLE II

| In Vitro Activity | | |
|---|---|---|
| | MIC/μg/ml. | |
| Test Organism | Fortimicin A Sulfate | 3-demethoxy-fortimicin A Tetrahydro-chloride |
| Staph. aureus Smith | 0.78 | 0.78 |
| Strep. faecalis 10541 | 50 | 25 |
| Enterobacter aerogenes 13048 | 3.1 | 3.1 |
| E. coli JUHL | 3.1 | 3.1 |
| E. coli BL 3676 (Res) | 25 | 25 |
| E. coli 76-2 | 3.1 | 1.56 |
| Kleb. pneumoniae 10031 | 1.56 | 1.56 |
| Kleb. pneumoniae KY 4262 | 6.2 | 3.1 |
| Providencia 1577 | 1.56 | 1.56 |
| Pseudo. aeruginosa BMH #10 | 0.78 | 0.78 |
| Pseudo. aeruginosa KY 8512 | 6.2 | 3.1 |
| Pseudo. aeruginosa KY 8516 | 6.2 | 3.1 |
| Pseudo. aeruginosa 209 | 100 | 100 |
| Pseudo aeruginosa 27853 | 12.5 | 6.2 |
| Sal. typhimurium Ed. #9 | 3.1 | 3.1 |
| Serratia marcescens 4003 | 3.1 | 1.56 |
| Shigella sonnei 9290 | 6.2 | 3.1 |
| Proteus rettgeri U6333 | 12.5 | 6.2 |

TABLE II-continued

| | In Vitro Activity | |
| | MIC/µg/ml. | |
| Test Organism | Fortimicin A Sulfate | 3-demethoxy-fortimicin A Tetrahydro-chloride |
| --- | --- | --- |
| *Proteus vulgaris* JJ | 3.1 | 3.1 |
| *Proteus mirabilis* Fin. #9 | 3.1 | 3.1 |

The overall activity of 3-demethoxyfortimicin A tetrahydrochloride is determined to be approximately 137% of that of fortimicin A sulfate, and on the order of 200% against many of the susceptible strains tested.

EXAMPLE 12

The procedure of Examples 1–10 is repeated using tri-N-benzyloxycarbonyl-3-O-demethylfortimicin B (see U.S. Pat. No. 4,124,756) as the starting material in place of the corresponding tetra-N-benzyloxycarbonyl-3-O-demethylfortimicin A of Example 1, to obtain 3-demethoxyfortimicin B tetrahydrochloride as the recovered product corresponding to the 3-demethoxyfortimicin A tetrahydrochloride of Example 10.

As is apparent from the foregoing, the compounds of formula I exhibit antibiotic activity against susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rettgeri, Proteus vulgaris* and *Proteus mirabilis*.

The compound of the invention may be used alone or in combination with a pharmaceutically acceptable carrier or diluent.

The compounds may be employed systemically by parenteral injection, e.g., by intramuscular, intravenous, intraperitoneal or subcutaneous routes of administration. The compounds can additionally be administered orally in those instances where it is desirable to sterilze the intestinal tract, and they can be administered topically and rectally. The compounds can also be incorporated into scrub solutions for reducing bacterial growth on such surfaces as laboratory bench tops, operating room surfaces and the like.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to inhibit growth of a susceptible organism for a particular composition and method of administration. The selected dosage level therefore depends upon the desired therapeutic effect, on the route of administration, on the duration of treatment and other factors. Generally, dosage levels of about 5 to about 200, more preferably about 10 to about 100 and most preferably about 15 to about 50 mg. of active ingredient per kg. of body weight are administered daily to a mammalian patient suffering from an infection caused by a susceptible organism. If desired, the daily dose may be divided into multiple doses for administration, e.g., two to four times per day.

What is claimed is:

1. A compound of the formula

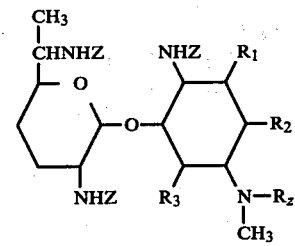

wherein $R_z$ is a monocyclicaryloxycarbonyl amine protecting group, or is loweralkyl, hydroxyloweralkyl, loweracyl, hydroxyloweracyl, or a monocyclicaryloxycarbonyl-protected aminoloweralkyl, diaminoloweralkyl, N-loweralkylaminoloweralkyl, N,N-diloweralkylaminoloweralkyl, aminohydroxyloweralkyl, N-loweralkylaminohydroxyloweralkyl, N,N-diloweralkylaminohydroxyloweralkyl, aminoloweracyl, diaminoloweracyl, N-loweralkylaminoloweracyl, N,N-diloweralkylaminoloweracyl, or aminohydroxyloweracyl; $R_1$ is hydroxy or loweracyloxy; $R_2$ is hydrogen or $-OR_4$, wherein $R_4$ is tert-butyldimethylsilyl or thiocarbonylimidazoyl; or $R_1$ and $R_2$ can be taken together to form

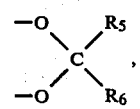

wherein $R_5$ and $R_6$ are loweralkyl; $R_3$ is hydroxy or loweracyloxy; and Z is a monocyclicaryloxycarbonyl amine protecting group.

2. A compound of claim 1 wherein Z is benzyloxycarbonyl.

3. A compound of claim 1 or 2 wherein $R_z$ is benzyloxycarbonyl.

4. A compound of claim 1 or 2 wherein $R_z$ is benzyloxycarbonyl-protected glycyl.

5. A compound of claim 1 or 2, wherein $R_1$ and $R_2$ are taken together to form

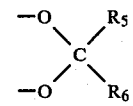

and wherein $R_5$ and $R_6$ are each methyl.

6. A compound of claim 5 wherein $R_3$ is hydroxyl.

7. A compound of claim 5 wherein $R_3$ is acetyl.

8. A compound of claim 1 or 2, wherein $R_3$ is acetyl.

9. A compound of claim 8 wherein $R_1$ is hydroxyl and $R_2$ is hydrogen.

10. A compound of claim 8 wherein $R_1$ is acetyl and $R_2$ is —$OR_4$, wherein $R_4$ is tert-butyldimethylsilyl or thiocarbonylimidazoyl.

11. A compound of claim 8 wherein $R_1$ and $R_3$ are acetyl and $R_2$ is hydrogen.

12. A compound of claim 1 or 2, wherein $R_1$ and $R_3$ are hydroxy and $R_2$ is hydrogen.

* * * * *